US00PP14821P2

(12) United States Plant Patent
Wood

(10) Patent No.: US PP14,821 P2
(45) Date of Patent: May 25, 2004

(54) PHYSOCARPUS PLANT NAMED 'SEWARD'

(50) Latin Name: *Physocarpus opulifolius*
Varietal Denomination: Seward

(75) Inventor: Timothy D. Wood, Grand Haven, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 10/624,100

(22) Filed: Jul. 21, 2003

(51) Int. Cl.[7] ..... A01H 5/00
(52) U.S. Cl. ..... Plt./226
(58) Field of Search ..... Plt./226

*Primary Examiner*—Kent Bell
(74) *Attorney, Agent, or Firm*—C. A. Whealy

(57) ABSTRACT

A new and distinct cultivar of Physocarpus plant named 'Seward', characterized by its upright and mounding plant habit; freely branching growth habit; and small dark purple-colored leaves with deep lobes and serration.

2 Drawing Sheets

Figure 1:
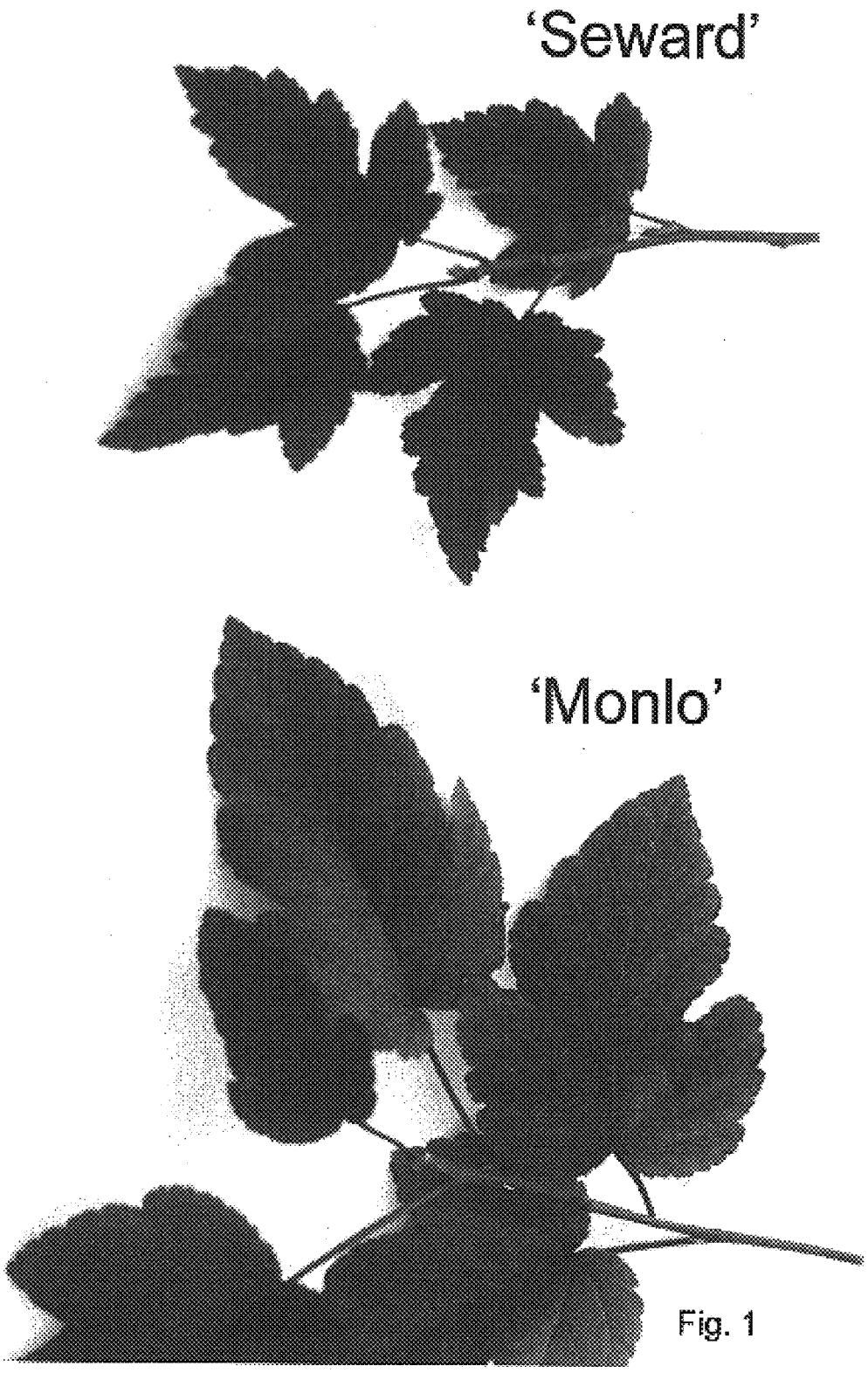
Figure 2:
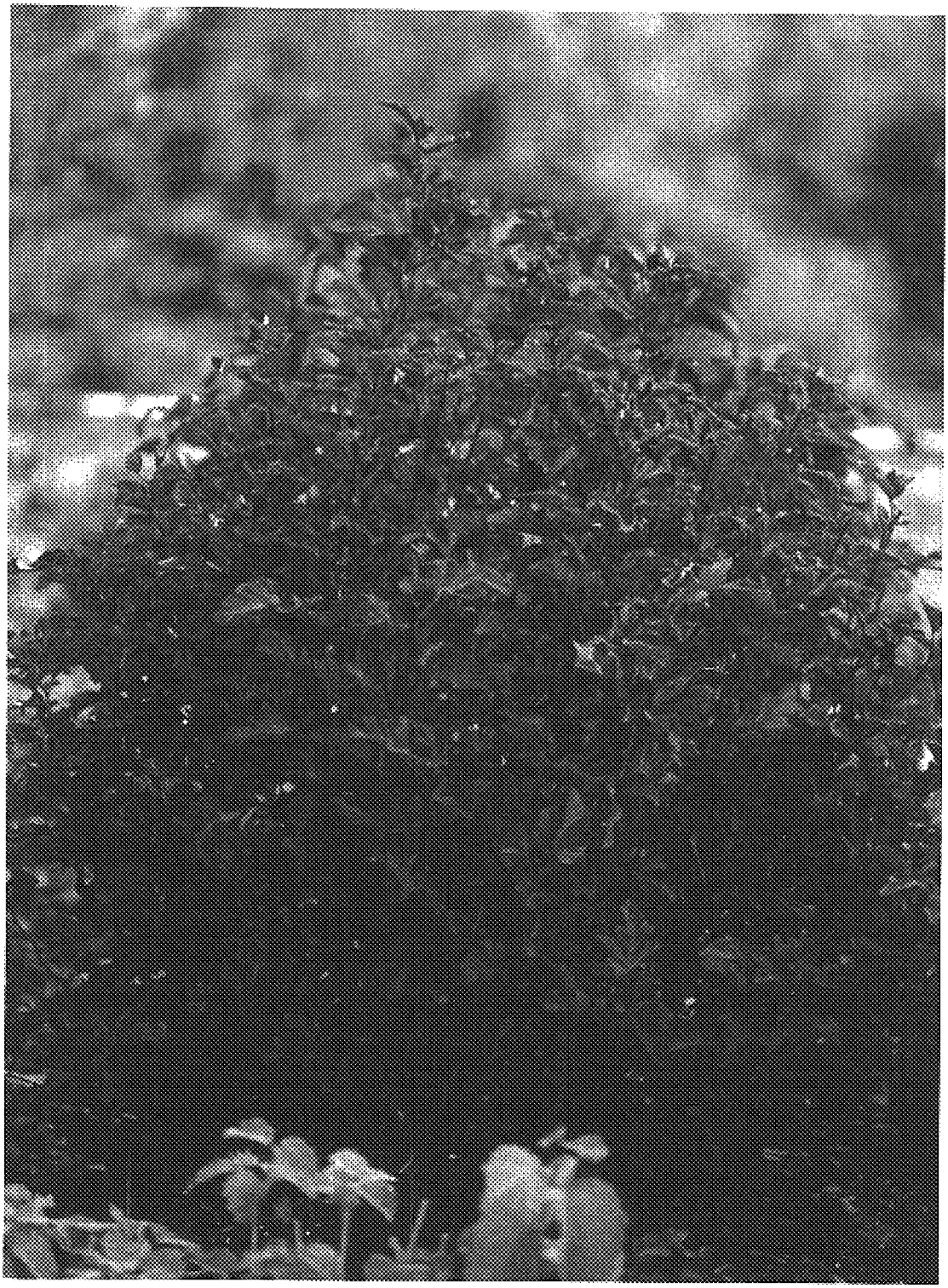

Botanical classification/cultivar designation: *Physocarpus opulifolius* cultivar Seward.

BACKGROUND OF THE INVENTION

The present Invention relates to a new and distinct cultivar of Physocarpus plant, botanically known as *Physocarpus opulifolius,* and hereinafter referred to by the name 'Seward'.

The new Physocarpus is a product of a breeding program conducted by the Inventor in Grand Haven, Mich. The objective of the breeding program was to create new compact and freely branching Physocarpus cultivars with small dark purple-colored leaves.

The new Physocarpus originated from a cross-pollination made by the Inventor in June, 2000, of the *Physocarpus opulifolius* var. Nanus, not patented, as the female, or seed, parent with the, *Physocarpus opulifolius* cultivar Monlo, disclosed in U.S. Plant Pat. No. 11,211, as the male, or pollen, parent. The new Physocarpus was discovered and selected by the Inventor as a single plant in a controlled environment in Grand Haven, Mich., within a population of the progeny resulting from the cross-pollination.

Asexual reproduction of the new Physocarpus by cuttings was first conducted in Grand Haven, Mich. in September, 2000. Since then, asexual reproduction by cuttings has shown that the unique features of this new Physocarpus are stable and reproduced true to type in successive generations.

SUMMARY OF THE INVENTION

The cultivar Seward has not been observed under all possible environmental conditions. The phenotype may vary somewhat with variations in environment such as temperature and light intensity without, however, any variance in genotype.

The following traits have been repeatedly observed and are determined to be the unique characteristics of 'Seward'. These characteristics in combination distinguish 'Seward' as a new and distinct Physocarpus:

1. Upright and mounding plant habit.
2. Freely branching growth habit.

3. Small dark purple-colored leaves with deep lobes and serration.

Plants of the new Physocarpus can be compared to plants of the female parent, the var. Nanus. In side-by-side comparisons conducted in Grand Haven, Mich., plants of the new Physocarpus differed from plants of the var. Nanus in the following characteristics:

1. Plants of the new Physocarpus were not as compact as plants of the var. Nanus.
2. Plants of the new Physocarpus had larger leaves than plants of the var. Nanus.
3. Leaves of plants of the new Physocarpus had dark purple-colored leaves whereas leaves of plants of the var. Nanus had green-colored leaves.

Plants of the new Physocarpus are most similar to plants of the male parent, the cultivar Monlo. In side-by-side comparisons conducted in Grand Haven, Mich., plants of the new Physocarpus differed from plants of the cultivar Monlo in the following characteristics:

1. Plants of the new Physocarpus were more compact than plants of the cultivar Monlo.
2. Plants of the new Physocarpus were more freely branching than plants of the cultivar Monlo.
3. Plants of the new Physocarpus had smaller leaves than plants of the cultivar Monlo.
4. Leaves of plants of the new Physocarpus had deeper lobes and were more undulating than leaves of plants of the cultivar Monlo.
5. Leaves of plants of the new Physocarpus were dark purple in color whereas leaves of plants of the cultivar Monlo were purple and green in color.

BRIEF DESCRIPTION OF THE PHOTOGRAPHS

The accompanying colored photographs illustrate the overall appearance of the new Physocarpus showing the colors as true as it is reasonably possible to obtain in colored reproductions of this type. Colors in the photographs may differ from the color values cited in the detailed botanical description which accurately describe the colors of the new Physocarpus.

The photograph on the first sheet is a close-up view of typical leaves of 'Seward' (top of sheet) and 'Monlo' (bottom of sheet).

The photograph on the second sheet comprises a side perspective view of a typical plant of 'Seward'.

DETAILED BOTANICAL DESCRIPTION

The aforementioned photographs and following observations and measurements describe two-year old plants grown in Grand Haven, Mich., in an outdoor nursery. During the production of the plants, day temperatures ranged from −20 to 30° C. and night temperatures ranged from −20 to 20° C. Color references are made to The Royal Horticultural Society Colour Chart, 1995 edition, except where general terms of ordinary dictionary significance are used.

Botanical classification: *Physocarpus opulifolius* cultivar Seward.

Parentage:

*Female, or seed, parent.*—*Physocarpus opulifolius* var. Nanus not patented.

*Male, or pollen, parent.*—*Physocarpus opulifolius* cultivar Monlo, disclosed in U.S. Plant Pat. No. 11,211.

Propagation:

*Type.*—By softwood cuttings.

*Time to initiate roots.*—About 15 days at 25° C.

*Time to produce a rooted plant.*—About 65 days at 25° C.

*Root description.*—Fibrous, white in color; freely branching.

Plant description:

*Appearance.*—Perennial deciduous shrub. Upright and mounding plant habit; rounded inverted triangle. Very freely branching; lateral branches potentially developing at every node; dense and full plants. Vigorous growth habit.

*Plant height.*—About 80 cm.

*Plant width or area of spread.*—About 100 cm.

*Lateral branches.*—Length: About 30 cm. Diameter: About 3 mm. Internode length: About 3 cm. Strength: Strong. Texture: Glabrous, smooth. Color: 187A.

*Foliage description.*—Arrangement: Alternate; simple. Length: About 5.5 cm. Width: About 5.5 cm. Shape: Roughly ovate; deeply lobed with three lobes per leaf. Apex: Acute. Base: Cordate to cuneate. Margin: Serrate. Venation pattern: Pinnate. Texture, upper and lower surfaces: Smooth, glabrous. Surface: Undulating. Color: Young foliage, upper surface: 187A. Young foliage, lower surface: 187B. Fully expanded foliage, upper surface: 187A to 187B. Fully expanded foliage, lower surface: 197A tinted with 187A. Venation, upper surface: 187A. Venation, lower surface: 197B. Petiole: Length: About 2 cm. Diameter: About 1 mm. Texture, upper and lower surfaces: Glabrous, smooth. Color, upper and lower surfaces: 187A.

Flower description:

*Appearance.*—Small single rotate flowers arranged in spherical corymbs. Flowers not persistent. Slightly fragrant.

*Natural flowering season.*—Plants flower during June and July in Grand Haven, Mich.

*Postproduction longevity.*—Individual flowers maintain good color and substance for about two to three weeks on the plant when grown in an outdoor environment.

*Flower bud.*—Length: About 3.5 mm. Diameter: About 3 mm. Shape: Elliptic. Color: 65D.

*Corymbs.*—Diameter: About 2.5 cm. Length: About 3.5 cm. Quantity of flowers per corymb: About 34.

*Flowers.*—Diameter: About 8 mm. Height (depth): About 6 mm.

*Petals.*—Quantity per flower: Five. Length: About 4.5 mm. Width: About 4.5 mm. Shape: Elliptic to obovate. Apex: Obtuse. Base: Attenuate. Margin: Entire. Texture, upper and lower surfaces: Smooth, glabrous. Color: Developing petals, upper surface: 155D. Developing petals, lower surface: 65C. Fully expanded petals, upper and lower surfaces: 155D; color becoming close to 197C with development.

*Sepals.*—Quantity per flower: Five. Calyx length: About 8 mm. Calyx diameter: About 8 mm. Shape: Subulate. Apex: Acute. Margin: Entire. Texture, upper and lower surfaces: Smooth, glabrous. Color, upper and lower surfaces: 144A.

*Peduncles.*—Length: About 1.3 cm. Diameter: About 1.5 mm. Strength: Flexible. Color: 144A.

*Reproductive organs.*—Stamens: Quantity per flower: Numerous, about 20 to 40. Anther shape: Oblong. Anther length: About 0.5 mm. Anther color: 46A. Pollen amount: Scarce. Pollen color: 46A. Pistils: Quantity per flower: About three or four. Pistil length: About 0.5 mm. Stigma shape: Globular. Stigma color: 145B. Style length: About 0.4 mm. Style color: 145B. Ovary color: 145D.

*Fruit/seed.*—Plants of the new Physocarpus have not been observed to produce fruit and seed.

Disease resistance: Plants of the new Physocarpus have been observed to somewhat resistant to Powdery Mildew.

Temperature tolerance: Plants of the new Physocarpus have been observed to tolerate temperatures from about −30 to 37° C.

It is claimed:

1. A new and distinct cultivar of Physocarpus plant named 'Seward', as illustrated and described.

* * * * *